United States Patent
Yeo

(10) Patent No.: US 10,441,582 B2
(45) Date of Patent: Oct. 15, 2019

(54) INJECTABLE ANTICANCER COMPOSITION FOR LOCAL ADMINISTRATION CONTAINING SUSPENSION OF QUININE SALT

(71) Applicant: Oh Young Yeo, Goyang-si (KR)

(72) Inventor: Oh Young Yeo, Goyang-si (KR)

( * ) Notice: Subject to any disclaimer, the term of this patent is extended or adjusted under 35 U.S.C. 154(b) by 62 days.

(21) Appl. No.: 15/498,212

(22) Filed: Apr. 26, 2017

(65) Prior Publication Data

US 2017/0360769 A1 Dec. 21, 2017

(30) Foreign Application Priority Data

Jun. 20, 2016 (KR) ........................ 10-2016-0076742

(51) Int. Cl.

| | | |
|---|---|---|
| *A61K 31/4709* | (2006.01) | |
| *A61K 31/16* | (2006.01) | |
| *A61K 9/00* | (2006.01) | |
| *A61K 31/525* | (2006.01) | |
| *A61K 49/04* | (2006.01) | |
| *A61K 47/22* | (2006.01) | |
| *A61K 9/10* | (2006.01) | |
| *A61K 31/167* | (2006.01) | |
| *A61K 47/02* | (2006.01) | |
| *A61K 31/49* | (2006.01) | |

(52) U.S. Cl.
CPC ........ *A61K 31/4709* (2013.01); *A61K 9/0019* (2013.01); *A61K 9/10* (2013.01); *A61K 31/167* (2013.01); *A61K 31/49* (2013.01); *A61K 31/525* (2013.01); *A61K 47/02* (2013.01); *A61K 47/22* (2013.01); *A61K 49/0438* (2013.01)

(58) Field of Classification Search
None
See application file for complete search history.

(56) References Cited

U.S. PATENT DOCUMENTS 8,506,973 B2 * 8/2013 Yeo ...................... A61K 9/0019
424/400

FOREIGN PATENT DOCUMENTS

| CN | 105560241 A | * | 5/2016 | |
|---|---|---|---|---|
| KR | 10-0390332 B1 | | 7/2003 | |
| KR | 10-2006-0034316 A | | 4/2006 | |
| KR | 10-2010-0137962 A | | 12/2010 | |
| KR | 10-1067443 B1 | | 9/2011 | |
| KR | 10-1208587 B1 | | 12/2012 | |
| WO | WO-2004004784 A1 | * | 1/2004 | ............. A61K 31/04 |

OTHER PUBLICATIONS

Srapra Technology, "Pharmaceutical Polymers" 2007, pp. 2 (Year: 2007).*
Wei, D., CN 105560241A English translation, accessed from: https://patents.google.com/patent/CN105560241A/en; accessed on Aug. 21, 2018; pp. 1-12 (Year: 2018).*
Feng, W., WO2004004784A1 English translation provided, accessed from: https://patents.google.com/patent/WO2004004784A1/en; accessed on Aug. 21, 2018, pp. 1-10 (Year: 2018).*
Balfour, A., "Review Recent Advances in Tropical Medicine", Dept. Education Sudan Gov. Khartoum,1908, pp. 115 (Year: 1908).*
Smith, F.A., et al., "Quinine Without Tetanus", Indian Medical Gazette, pp. 333-336 (Year: 1911).*
Hare, H.A., et al., "Progressive Medicine", Lea and Febiger, p. 394 (Year: 1923).*

* cited by examiner

*Primary Examiner* — Michael G. Hartley
*Assistant Examiner* — Lance W Rider
(74) *Attorney, Agent, or Firm* — KORUS Patent, LLC; Seong Il Jeong

(57) ABSTRACT

Disclosed herein is an injectable anticancer composition for local administration, which contains a suspension of quinine hydrochloride. The anticancer composition for local administration according to the present invention shows an $IC_{50}$ value against MKN-45 cells, which is about 10 times lower than Paclitaxel, as determined by an MTT assay in vitro, suggesting that the anticancer composition has an excellent cytotoxic effect. The anticancer composition can be administered as a safe anticancer agent in clinical applications, and also shows an anticancer effect by inducing the necrosis and detachment of solid cancer cells. Particularly, the anticancer composition has an anticancer mechanism by which the composition acts locally in a tumor tissue administered with the composition and shows a rapid antitumor effect (1-2 weeks after administration).

3 Claims, 7 Drawing Sheets

INJECTABLE ANTICANCER COMPOSITION FOR LOCAL ADMINISTRATION CONTAINING SUSPENSION OF QUININE SALT

BACKGROUND

1. Technical Field

The present invention relates to an anticancer composition containing a suspension of a quinine salt compound, and more particularly to an injectable composition for local administration containing a suspension of a quinine salt compound as a main compound, which is injected directly into cancer cells to exhibit an anticancer effect of inducing necrosis of the cancer cells.

2. Description of the Related Art

Generally, tumors are diseases in which abnormal cells proliferate uncontrollably and interfere with the function of normal cells. Tumors are classified according to histopathological and clinical criteria into malignant tumors and benign tumors, and the so-called cancer belongs to malignant tumors.

Cancer is the first leading cause of death in Korea, and is also a leading cause of death worldwide. The cause of development of cancer or a method for treatment of cancer has not yet been clearly elucidated. Cancer therapeutic agents that have been developed to date show problems associated with fatal side effects, expression of drug resistance, destruction of lymphocytes and bone marrow, etc., when they are clinically used. Due to such side effects, the cancer therapeutic agents show symptoms, such as weight loss, hair loss, etc.

Accordingly, there is an urgent need to develop novel anticancer agents that exhibit selective cytotoxic activity against cancer cells without affecting normal cells.

Up to now, about 270 kinds of cancer have been found to occur in the human body. Cell lines reported to be used in research of these kinds of cancer include gastric cancer cells (MKN-45), sarcoma cells (Sarcoma-180), melanoma cells, adenoma cells, adeno-carcinoma cells, Ehrlich ascites tumor cells and Walker carcinoma cells.

Meanwhile, quinine is widely known as an antimalarial agent, and is currently being used for treatment of rheumatoid arthritis, discoid and systemic lupus erythematosus, photosensitive skin diseases. Recently, studies on quinine for the suppression of renal injury and the treatment of malignant glioma have been reported.

In addition, quinine is known to inhibit cellular activity and serve as an antipyretic.

Korean Patent No. 10-0390332 discloses an anticancer composition which allows an anticancer agent, such as doxorubicin or cisplatin, to be co-administered with hydroxychloroquine, chloroquine, primaquine or the like, which is frequently used as an antimalarial agent, thereby reducing the 50% inhibitory concentration ($IC_{50}$) of the anticancer agent and inhibiting the drug resistance of cancer cells caused by the anticancer agent.

In this case, the antimalarial agent, such as hydroxychloroquine, is used as an adjuvant to inhibit the resistance of cancer cells against the anticancer agent so as to increase the anticancer effect of the anticancer agent, and the anticancer agent exhibits its effects by systemic administration via various routes, such as oral and parenteral routes.

Furthermore, Korean Unexamined Patent Application Publication No. 10-2006-0034316 (published on Apr. 24, 2006) discloses an injectable sclerosing agent for treatment of hemorrhoids, which contains quinine, borneol, a gallnut extract, and a licorice extract.

In the above patent application publication, a description of cancer treatment with a quinine salt or the description of pharmacological effect of the quinine salt cannot be found.

In addition, the applicant has acquired patents relating to an injectable composition for local administration for treatment of hemorrhoids (Korean Patent No. 10-1067443) and an injectable anticancer composition for local administration (Korean Patent No. 10-1208587), which contain hydroxychloroquine.

According to the above Korean Patents acquired by the applicant, hydroxychloroquine is effective in the treatment of hemorrhoids and cancer. However, there are problems in that hydroxychloroquine is water-soluble, and thus it spreads to normal cells surrounding hemorrhoids or cancer cells to cause a significant problem associated with systemic toxicity, is difficult to administer at high concentration, and induces necrosis of normal cells.

SUMMARY

The present invention has been made in order to solve the above-described problems occurring in the prior art, and it is an object of the present invention to provide an anticancer composition for local administration, which contains a suspension of a poorly water-soluble quinine salt so as to act selectively against cancer cells in a affected area to induce necrosis of the cancer cells without affecting normal cells surrounding the affected area. Particularly, it is an object of the present invention to provide an anticancer composition for local administration, which has selective cytotoxicity against cancer cells without spreading throughout the human body, and which is to be injected directly into cancer cells.

To achieve the above object, the present invention provides an injectable anticancer composition for local administration, which contains a suspension of a quinine salt as a substitute for hydroxychloroquine.

When an injectable suspension of water-insoluble quinine hydrochloride is to be administered, it may be administered after dissolution in a solvent. In this case, there is a problem in that because the concentration of quinine hydrochloride in use for anticancer therapy is strictly limited due to its systemic toxicity, it is impossible to topically administer a high concentration of quinine hydrochloride for tumor cell growth inhibition and tumor tissue necrosis.

However, in order to solve this problem, the present inventor changed a suspension of quinine hydrochloride into a solvent-free injectable solution formulation based on the physical properties of quinine hydrochloride so as to enable quinine hydrochloride to be administered topically at high concentrations and act locally. Moreover, the present inventor administered the injectable solution formulation to tumor tissue, and as a result, shown that the injectable solution formulation changed to a solid state in the tumor tissue and acted selectively on the tumor cells without affecting the whole body. Accordingly, the present inventor could develop an anticancer drug which might be administered topically at high concentrations and which acted locally.

Therefore, the present invention provides a method for preparing an injectable suspension, comprising changing a suspension composition comprising a quinine hydrochloride into a solvent-free injectable solution formulation so as to enable the quinine hydrochloride to be administered topically at high concentrations and act locally.

In the method, the suspension may be heated to a temperature of 40° C. or higher.

The injectable composition according to the present invention acts to induce necrosis of cells in an affected area by inhibiting the proliferation and metabolism of malignant tumors (cancer cells) and abnormal cells (e.g., benign tumors).

Hydroxychloroquine, a derivative of quinine, is widely known to be used as an antimalarial agent, an anti-rheumatoid agent, etc., and to have a pharmacological mechanism similar to that of a quinine salt.

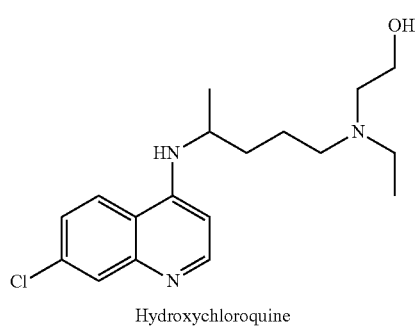 [SMILES: CCN(CCO)CCCC(C)Nc1ccnc2cc(Cl)ccc12]

Hydroxychloroquine

However, hydroxychloroquine is water-soluble, and thus when it is administered to a affected area, it will spread not only to the affected part, but also to normal cells of the whole cells, so that the in vivo systemic toxicity will increase 100-fold to several hundred-folds, thus increasing the risk of hydroxychloroquine administration for treatment, and it will cause an adverse effect to induce necrosis of normal cells. To overcome such problems, in the present invention, a quinine salt which is poorly water-soluble is used as a substitute for hydroxychloroquine.

Examples of the quinine salt that is used in the present invention include quinine hydrochloride, quinine sulfate, quinine phosphate, and the like.

For example, quinine hydrochloride has the following structural formula:

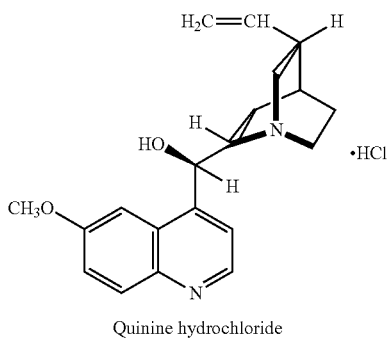

Quinine hydrochloride

The quinine salt compound has a melting point of 57° C., is well soluble in organic solvents such as ethyl alcohol. However, it is poorly soluble in water, and thus exists as a suspension or a solid at room temperature. The suspension dissolves into a solution at a certain temperature depending on the concentration of the quinine salt.

TABLE 1

Change in temperature of formulation with change in concentration of quinine salt

| | Concentration | | |
|---|---|---|---|
| | 10% | 30% | 50% |
| Solution | 38° C. | 46° C. | 57° C. |
| Suspension | 35° C. | 43° C. | 43° C. |
| Solid | 34° C. | 38° C. | 38° C. |

Based on the temperature at which the quinine salt dissolves in water, the present inventor has solved the problems of the conventional injectable formulation containing hydroxychloroquine.

The quinine salt that is used in the present invention is not well soluble in water, and dissolves in hot water to form a homogeneous solution.

Namely, when a suspension of the quinine salt, which dissolves at a temperature equal to or higher than 36° C. (which is the human body temperature), is used as an injectable solution and when it is injected into a affected area of the human body after its dissolution at a temperature higher than the human body temperature, the temperature of the solution will be reduced below its crystallization temperature by the human body temperature, so that the solution will be converted to a suspension or solid in the tissue to thereby minimize the systemic migration of the quinine salt. Accordingly, the quinine salt will no longer spread in the human body, will block blood cell metabolism and cellular physiological metabolism and will interfere with the metabolism of the cells in the affected area. Accordingly, when the injectable solution is administered, it will harden cells surrounding the administered area to induce selective necrosis of the affected area administered with the injectable solution, but will not spread to normal cells surrounding the affected area and not affect the normal cells.

Although the quinine salt solution apparently looks like a solution, it is a suspension in which the quinine salt is homogeneously suspended in physiological saline. When the quinine salt solution is injected into a affected area, the physiological saline will be absorbed into cells to rapidly increase the concentration of the quinine salt, and the solution will harden into a solid state to thereby block cellular physiological metabolism, and will exhibit a pharmacological activity of inducing necrosis of cancer cells by the anticancer activity of the quinine salt.

Accordingly, it is also possible to use an injectable formulation comprising a low-concentration quinine salt suspension, which is crystallized at a temperature equal to or lower than the human body temperature.

Therefore, the injectable composition according to the present invention can overcome the problem of the conventional hydroxychloroquine-containing injectable formulation that spreads not only to a affected area, but also to normal cells of the human body to induce necrosis of the normal cells, due to the water solubility of the hydroxychloroquine formulation.

The injectable composition comprising the quinine salt suspension according to the present invention is useful against solid cancers, such as skin cancer, other than systemic cancer.

The anticancer composition according to the present invention may be injected directly into a affected area such as cancer cells, and preferably further contains a local anesthetic such as lidocaine and/or an antioxidant such as riboflavin.

The injectable composition according to the present invention may further contain a contrast agent or a fluorescent probe so as to trace the blockage of blood cell metabolism and the uptake, metabolism and metabolism of the drug after in vivo administration of the composition. In addition, it may further contain an adhesive agent that allows the quinine salt to be attached to the affected area when the quinine salt is crystallized in the affected area.

The contrast agent or fluorescent probe that is used in the present invention is a component that is generally used for medical purposes, and it is preferably contained in an amount of 0.01-0.2% (w/w) based on the total weight of the composition.

In the present invention, the composition for local administration comprising the quinine salt suspension is administered directly to an affected area, such as malignant tumor or abnormal cell tissue (cancer cells or malignant tumor), to block blood cell metabolism and physiological metabolism of cancer cells to thereby harden the affected tissue so as to be necrotized.

The metabolism of cancer cells is faster than that of normal cells, and for this reason, when the activity of cancer cells is inhibited by the quinine salt suspension and the metabolism of cancer cells is blocked by the quinine salt suspension, the cancer cell tissue will be inactivated so that the proliferation of the cancer cells will be inhibited and supply of nutrients to the cancer cells will be blocked, resulting in the necrosis of the cancer cell tissue.

A test for the anticancer activity of the quinine salt suspension in the composition of the present invention indicated that the suspension showed uniform physical and biochemical properties and effects regardless of the concentration of the quinine salt (see FIGS. 6, 7 and 8).

Accordingly, the composition of the present invention may be administered after adjustment of the concentration of the quinine salt depending on the severity of the patient to be subjected to anticancer treatment.

Namely, in an acute state, the composition is preferably at a high quinine salt concentration for quick treatment effects. For relatively mild and slow treatment, the composition is preferably administered several times at a low quinine salt concentration.

Accordingly, the content of the quinine salt in the composition of the present invention is particularly limited. However, in view of the intended use and efficacy of the injectable composition, the quinine salt is preferably contained in an amount of 4-60% (w/w), more preferably 10-50% (w/w).

If the content of the quinine salt in the composition is less than 4% (w/w), an inconvenience will arise in that the number of administrations of the composition needs to be increased for pharmacological activity, and if the content of the quinine salt in the composition is more than 60% (w/w), the injectable composition will be difficult to administer, due to its high viscosity.

A solvent that is used in the present invention is sterile physiological saline that is generally used for injection applications.

In the injectable composition for local administration according to the present invention, the local anesthetic serves to alleviate pain occurring due to the composition temperature higher than the human body temperature when the composition is administered by injection directly into cancer cells. As the local anesthetic, lidocaine is preferably used at a concentration of 1-2% (w/w).

Furthermore, the antioxidant serves to stabilize the composition. As the antioxidant, riboflavin is used at a concentration of 0.1-0.5% (w/w).

The contrast agent or the fluorescent probe is preferably contained in an amount of 0.01-0.2% (w/w) based on the total weight of the composition.

The injectable anticancer composition for local administration according to the present invention may be prepared according to any conventional method for preparing injectable formulations.

The injectable anticancer composition for local administration according to the present invention is preferably injected directly into cancer cells. The composition of the present invention may be repeatedly administered at intervals of 3-4 days for several weeks depending on the patient's conditions or may be repeatedly administered at intervals of 1-2 days depending on the size and progression of cancer cells, whereby it can inhibit the proliferation and metabolism of cancer cells to inactivate the cancer cells within a short time.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
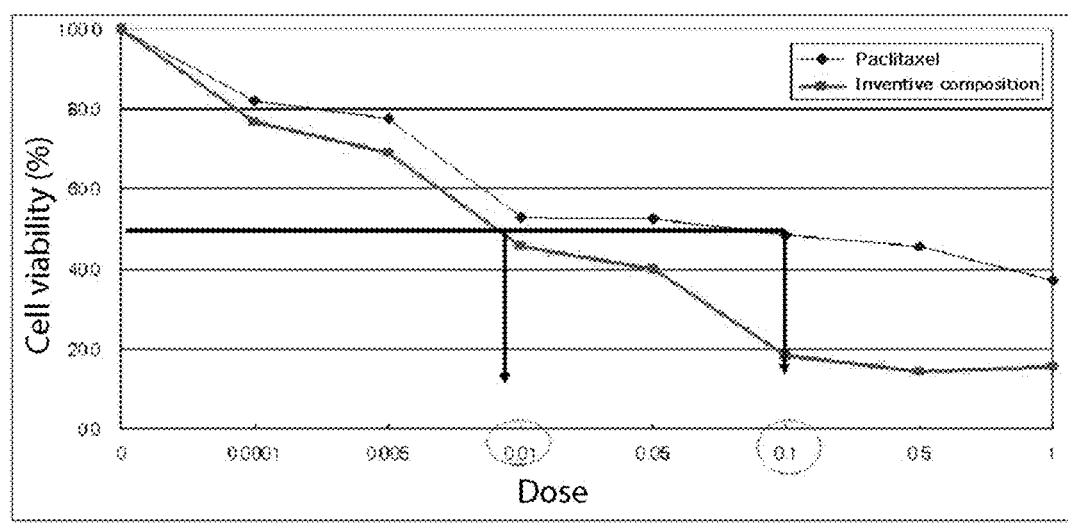
FIG. 1 is a graph showing the results of evaluating the effect of the composition of the present invention on the growth of the MKN-45 cell line in comparison with a control drug by an MTT assay.

The present invention will be described in detail with reference to examples below. However, these examples are illustrative, and the scope of the present invention is not limited only to these examples.

Test Method (1) Drugs for Administration

The quinine salt suspension composition of the present invention, which was used in this test, was prepared as a 50% (w/w) suspension of quinine hydrochloride for local administration, which would be injected directly into cancer cells, by using quinine chloride as the quinine salt.

Specifically, 50 g of quinine chloride, 1.5 g of lidocaine, 0.15 g of riboflavin and 0.1 g of a contrast agent Tomoray 320, Dongkook Pharmaceutical, Co., Ltd., Korea) were mixed with one another, and 48.25 ml of physiological saline for injection was added to the mixture, thereby preparing an injectable suspension.

For use as an injectable solution, the suspension was dissolved by heating it to 60° C. on a water bath, and was then injected into an affected area.

Paclitaxel used as a positive control drug was purchased from Vspharm Co., Ltd.

(2) Cancer Cell Line

The cancer cell line used in this Example was MKN-45 obtained from the Korean Cell Line Bank.

Culture of the MKN-45 cell line was performed by the Nonclinical Research Institute of Chemon Inc. (Korea). The MKN-45 cell line was subcultured with RPMI1640 medium (supplemented with L-glutamine and 10% FBS) in a 5% $CO_2$ incubator at 37° C. for 48 hours, and was then used in the test.

For animal tests, the MKN-45 cell line was injected into the abdominal cavity of BALB/c nude at a concentration of $5 \times 10^6$ cells/100 µL. After about 2 weeks, the ascites was collected and centrifuged at 2000 rpm, and the precipitate was washed twice and then stained with 0.4% trypsin blue, thereby obtaining $5 \times 10^6$ cells/100 µL.

(3) Test Animals

Fifty 5-week-old BALB/c nude mice (produced by Central Lab Animal Inc., Korea) were purchased and acclimated for 1 week before use in the test. The animals were housed in Room No. 2 of the Animal Breeding Zone of the GyeongGi Bio Center (Korea) under the following conditions: a temperature of 23±3° C.; a relative humidity of 55±15%; 10-20 ventilations/hr; an illumination time (lighting at 8 a.m. and lighting-out at 8 p.m.); and an illumination intensity of 150-300 Lux.

The mice weighed 18.67-23.19 g upon the start of administration.

Example 1

Measurement of Cytotoxicity Against MKN-45 Cells

In order to evaluate the effect of the composition of the present invention on cytotoxicity, an MTT assay was used.

The MTT assay is a laboratory test method for measuring cell viability, and can be regarded as a standard colorimetric assay.

The MTT assay capable of accurately measuring the proliferation of cells and the number of living cells is an essential technique in the bioscience field, particularly the tumor biology field.

Before in vivo tests, such as animal tests, are carried out in order to search effects for the development of novel anticancer drugs or to examine the sensitivity of existing anticancer drugs, a process of objectively demonstrating that the drugs inhibits the growth of tumors ex vivo should be carried out.

The cell line prepared in (2) above was added to each well. Also, the composition of the present invention was diluted in ethyl alcohol to a total of 8 concentrations (1.0 µg/mL, 0.5 µg/mL, 0.1 µg/mL, 0.05 µg/mL, 0.01 µg/mL, 0.005 µg/mL, 0.0001 µg/mL, and 0 µg/mL) (see FIG. 1) and added to each well, and Paclitaxel was also diluted in the same manner as above and added to each well.

Then, the cells were cultured in a 5% $CO_2$ incubator at 37° C. for 24 hours, and 50 µL of MTT reagent was added thereto at a concentration of 2 mg/mL. Then, the cells were incubated in an incubator at 37° C. for 4 hours.

The cell culture was centrifuged to remove the supernatant, and 200 µL of DMSO was added to each well to dissolve the MTT-stained precipitate, after which the $OD_{540}$ value at a wavelength of 540 nm was measured with an ELISA reader.

The 50% inhibitory concentration ($IC_{50}$) was defined as the drug concentration that resulted in 50% of cell viability, and the $IC_{50}$ value was used as an index of the anticancer effect of the drug.

FIG. 1 is a graph showing the results of evaluating the effect of the composition of the present invention on the growth of the MKN-45 cell line in comparison with a control drug by an MTT assay.

The composition of the present invention was added to the MKN-45 cell line suspension, and then the anticancer activity thereof was compared with the control drug Paclitaxel. As a result, as can be seen in FIG. 1, the $IC_{50}$ value of the composition of Paclitaxel was shown at 0.1 µg/mL, whereas the $IC_{50}$ value of the composition of the present invention was shown at 0.01 µg/mL or less.

In other words, the $IC_{50}$ value of the quinine hydrochloride suspension of the present invention against MKN-45, determined by the MTT assay in vitro, was about 10 times lower than that of Paclitaxel, suggesting that the quinine hydrochloride suspension of the present invention has an excellent cytotoxic effect.

Example 2

Effect of Inventive Injectable Composition on Change in Cancer Cell Growth

In order to observe the anticancer activity of the composition of the present invention in BALB/c nude, the BALB/c nude were inoculated with MKN-45 cells, and then the effect of the composition of the present invention on the differentiation of the MKN-45 cells was evaluated.

Specifically, as shown in Table 2 below, animals acclimated to housing facilities were divided into a total of 5 groups (G1 to G5), each consisting of 8 animals.

Table 2 below shows the establishment of test groups and the drug concentration.

TABLE 2

| Group | Sex | Number of animals | Animal No. | Volume of suspension administered (μL/head) | Dose (mg/head) | Substance administered | Route of administration |
|---|---|---|---|---|---|---|---|
| G1 | M | 8 | 1-8 | 50 | — | — | i.t |
| G2 | M | 8 | 9-16 | 50 | 12.5 | Quinine hydrochloride | i.t |
| G3 | M | 8 | 17-24 | 50 | 25 | Quinine hydrochloride | i.t |
| G4 | M | 8 | 25-32 | 50 | 50 | Quinine hydrochloride | i.t |
| G5 | M | 8 | 33-40 | 10 mL/kg | 20 mg/kg | Paclitaxel | i.v |

G1: untreated group (vehicle control group; PBS)
G2 to G4: groups administered with the injectable composition of the present invention
G5: group administered with the control anticancer drug (Paclitaxel)

MKN-45 cells were transplanted by subcutaneous injection into the right flank of all the groups at a concentration of $5 \times 10^6$ cells/100 μL/head, thereby inducing solid cancer. When the tumor mass of the transplanted cells reached about 150-200 mm$^3$, the animals were uniformly grouped, and the composition of the present invention was set at low dose (12.5 mg/head), medium dose (25 mg/head) and high dose (50 mg/head), and each dose of the composition was administered to the mice three times at 3-day intervals. The general symptoms, body weight changes, tumor volumes and tumor weights of the groups administered with the composition of the present invention were evaluated and compared with those of the vehicle control group and the control group (Paclitaxel).

In the first administration, a suspension volume of 50 μL/head was used regardless of body weight.

From the second administration, a high dose of 50 mg/head (as prepared), a medium dose of 25 mg/head and a low dose of 12.5 mg/head were used.

The medium dose used was a 2-fold dilution of the prepared injectable suspension, and the low dose used was a 4-fold dilution of the prepared injectable suspension.

The injectable suspension was dissolved by heating to a temperature of 42 to 45° C. on a water bath. Next, 20 μL of the solution was administered to the apex of the tumor by means of a 0.3 mL insulin syringe, and 10 μL of the solution was administered to each of three points of the bottom side of the tumor. Accordingly, a total of 50 μL of the solution was administered to the tumor.

The results of observation of the general symptoms are as follows. In the vehicle control group (G1), weight loss was observed from day 16. In the group (G2) administered with 12.5 mg/head of the injectable suspension of the present invention, one weight loss case on day 1, four tumor detachment cases and three partial necrosis cases on day 16, one weight loss case on each of day 18 and day 19, and two re-tumorigenesis cases on day 24, were observed.

In the group (G3) administered with 25 mg/head of the injectable suspension of the present invention, two tumor detachment cases and five particle necrosis cases were observed on day 16, and one weight loss case was observed on day 18, and two re-tumorigenesis cases were observed on day 24.

In the group (G4) administered with 50 mg/head of the injectable suspension of the present invention, one dull case and one weak case on day 1, four partial necrosis cases on day 16, and one re-tumorigenesis case on day 24, were observed. It is believed that the re-tumorigenesis occurred in cancer cell regions which were not affected by the injectable suspension of the present invention.

Figure 2:
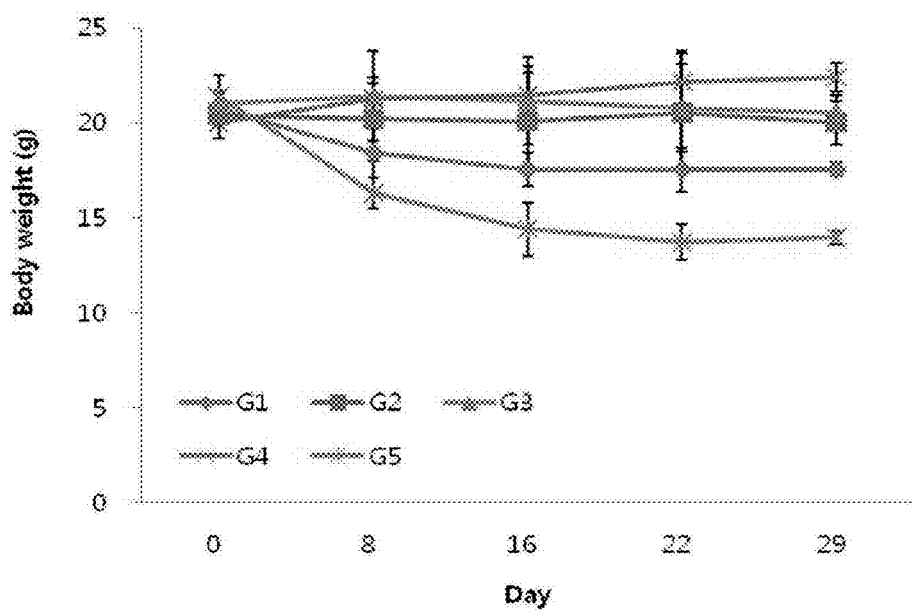
FIG. 2 is a graph showing the effect of the composition of the present invention on changes in the body weights of BALB/c nude mice in comparison with a control drug.

FIG. 2 is a graph showing the changes in body weight of BALB/c nude mice caused by the composition of the present invention in comparison with the vehicle control group (G1) and the control drug group (G5). The data are expressed as mean±S.D. The results were statistically analyzed by ONE-WAY ANOVA and Student's t-test methods.

As shown in FIG. 2, the decrease in body weight by administration of the composition of the present invention was not observed, but a significant decrease in body weight appeared in the vehicle control group (G1) and the control drug group (G5). It appears that this decrease in body weight occurred due to the weakness caused by the proliferation of cancer cells (G1) and due to the toxicity of the drug (G5).

Accordingly, it can be seen that the composition exhibits an anticancer effect by inducing the necrosis and detachment of cancer cells, the systemic toxicity thereof is insignificant.

As an index of the anticancer effect of the injectable suspension according to the present invention, the mean volume of the tumors of each group was measured on different days. On the final day of the test, the animals were biopsied and visually observed, and the mean weight of the tumors was measured. As a result, it was shown that the volume and weight of the tumors were significantly reduced.

Figure 3:
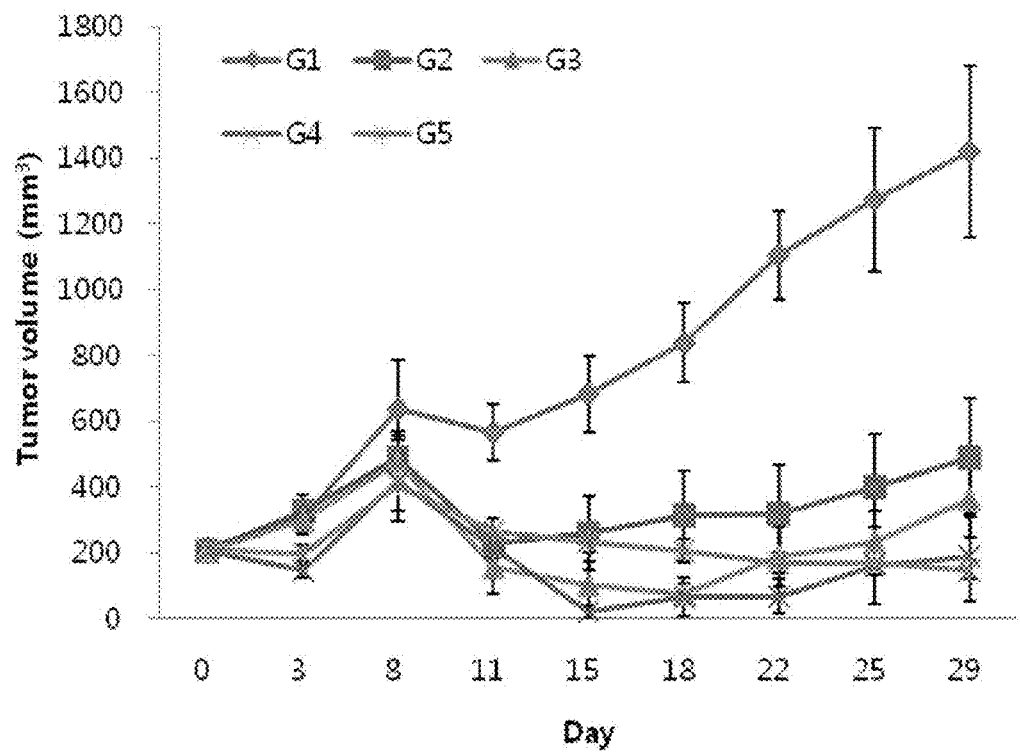
FIG. 3 is a graph showing the effect of the composition of the present invention on changes in the volume of a solid tumor of MKN-45 cells in BALB/c nude mice in comparison with a control drug.

FIG. 3 is a graph showing the effect of the composition of the present invention on the tumor volume of a solid tumor of MKN 45 cells in BALB/c nude mice. The data are expressed as mean±S.E.M. The results were statistically analyzed by ONE-WAY ANOVA and Student's t-test methods.

In FIG. 3, G1 is an untreated group; G2 is a group administered with 15 mg/head of the present invention; G3 is a group administered with 25 mg/head of the present invention; G4 is a group administered with 50 mg/head of the present invention; and G5 is a group administered with a control drug (Paclitaxel).

The results of measurement of the tumor volume indicated that the groups (G2 and G3) administered with 12.5 mg/head and 25 mg/head of the composition of the present invention showed a statistically significant decrease in the tumor volume from day 8, compared to the vehicle control group (G1).

Moreover, it was shown that the group (G4) administered with 50 mg/head of the composition of the present invention showed a statistically significant decrease in the tumor volume from day 3, compared to the vehicle control group (G1).

Figure 4:
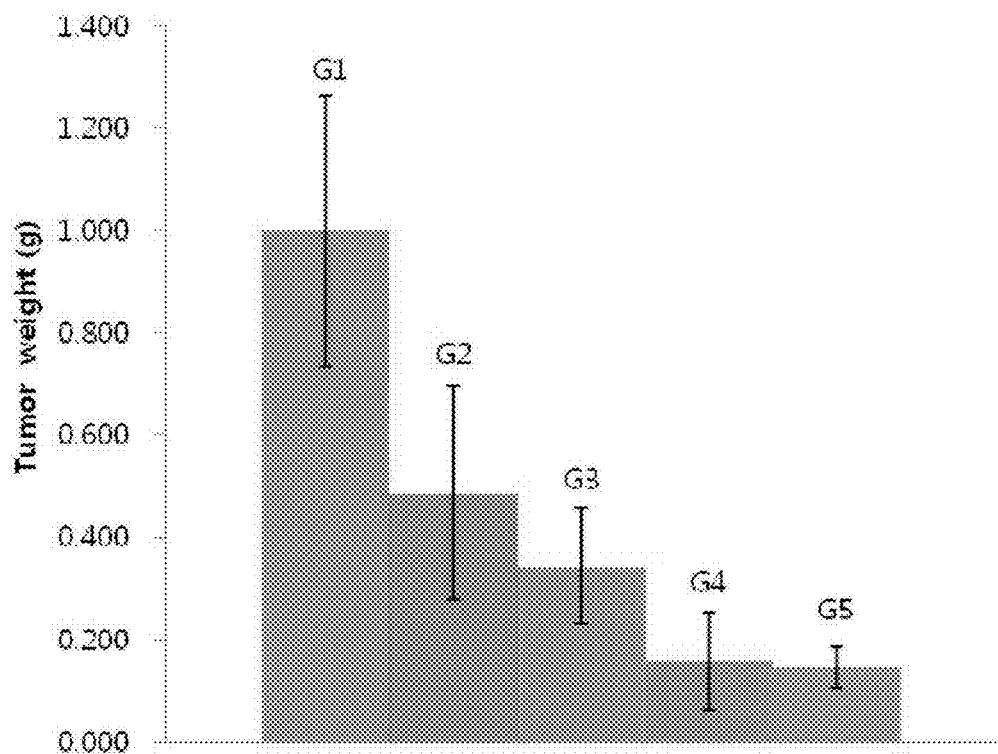
FIG. 4 is a graph showing the effect of the composition of the present invention on changes in the weight of a solid tumor of MKN-45 cells in BALB/c nude mice in comparison with a control drug.

FIG. 4 is a graph showing the effect of the composition of the present invention on the tumor weight of a solid tumor of MKN 45 cells in BALB/c nude mice. The data are expressed as mean±S.E.M. The results were statistically analyzed by ONE-WAY ANOVA and Student's t-test methods.

The results of measurement of the tumor weight indicated that the groups (G2, G3 and G4) administered with 12.5, 25 and 50 mg/head of the composition of the present invention showed a statistically significant decrease in the tumor weight compared to the vehicle control group (G1).

Figure 5:
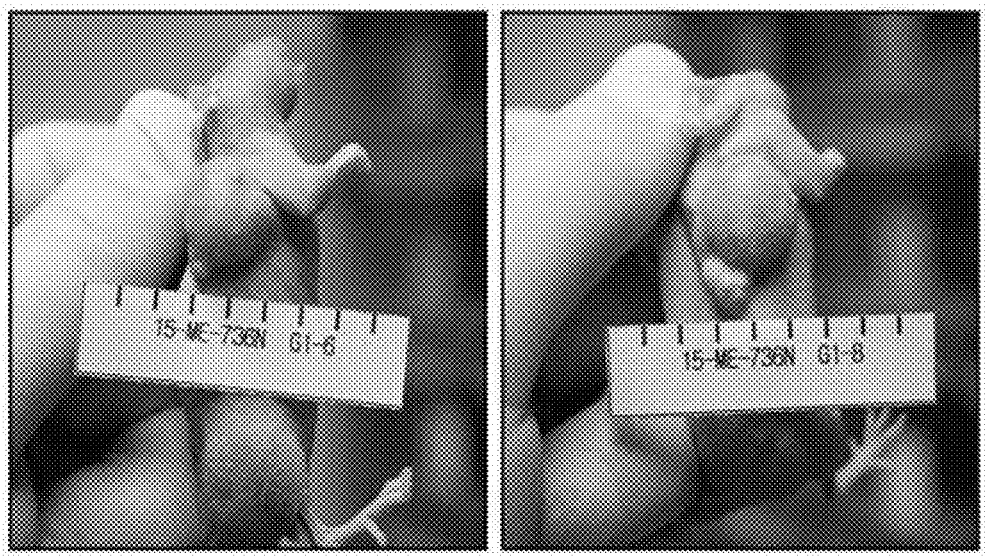
FIG. 5 depicts photographs showing solid tumors induced by MKN-45 cells in BALB/c nude mice of a vehicle control group (G1)

FIG. 5 depicts photographs showing solid tumors induced by MKN 45 cells in BALB/c nude mice of the vehicle control group (G1).

Figure 6:
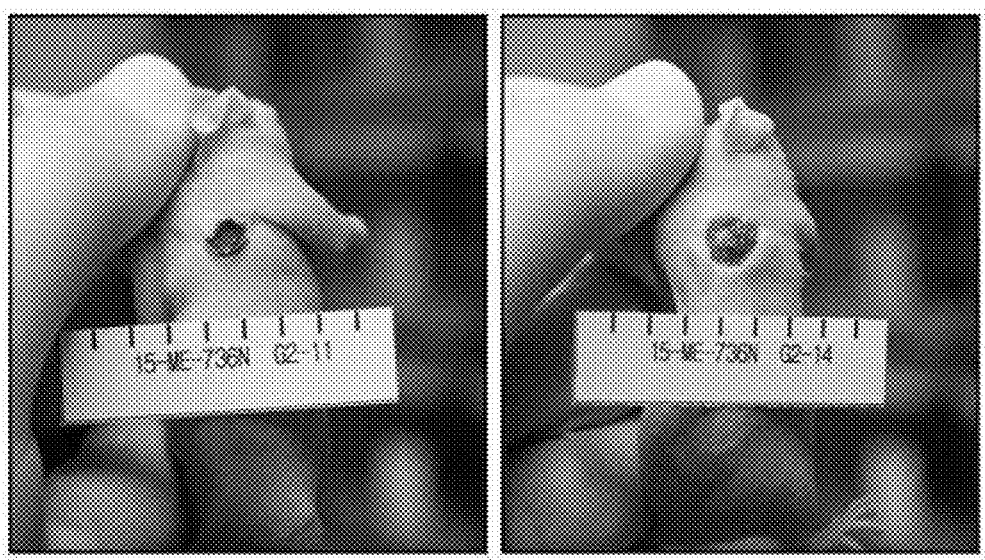
FIG. 6 depicts photographs showing that solid tumors of MKN-45 cells in BALB/c nude mice were necrotized and detached 2 weeks after administration of 12.5 mg/head of the injectable suspension of the present invention (G2)

FIG. 6 depicts photographs showing that solid tumors of MKN 45 cells in BALB/c nude mice were necrotized and detached 2 weeks after administration of 12.5 mg/head of the injectable suspension of the present invention (G2).

Figure 7:
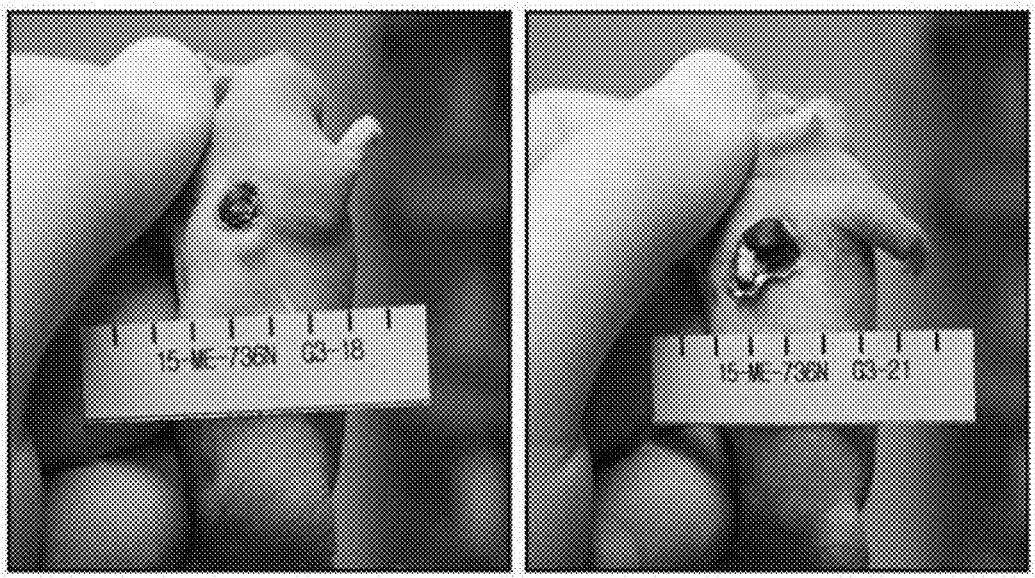
FIG. 7 depicts photographs showing that solid tumors of MKN-45 cells in BALB/c nude mice were necrotized and detached 2 weeks after administration of 25 mg/head of the injectable suspension of the present invention (G3)

FIG. 7 depicts photographs showing that solid tumors of MKN 45 cells in BALB/c nude mice were necrotized and detached 2 weeks after administration of 25 mg/head of the injectable suspension of the present invention (G2).

Figure 8:
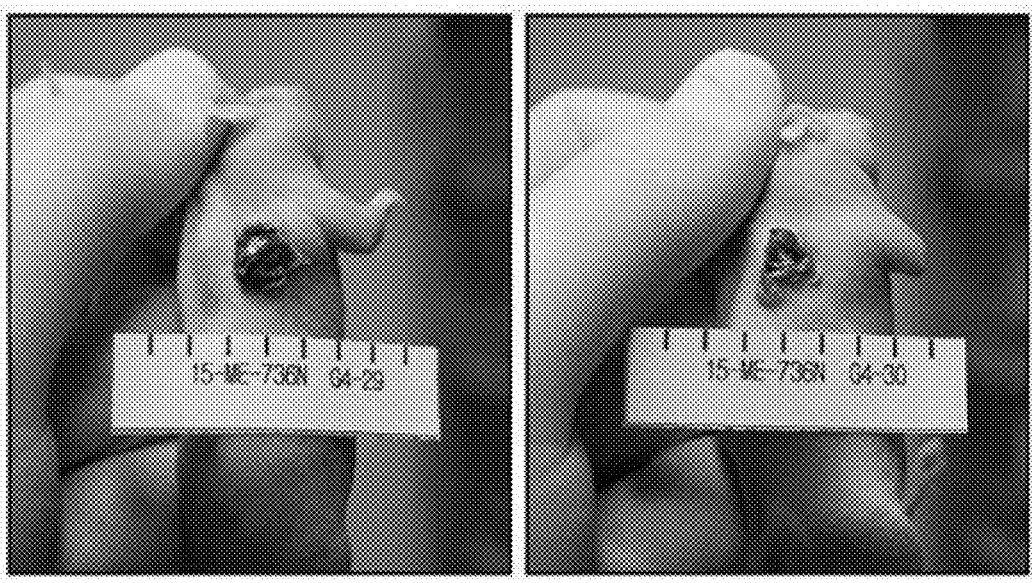
FIG. 8 depicts photographs showing that solid tumors of MKN-45 cells in BALB/c nude mice were necrotized and detached 2 weeks after administration of 50 mg/head of the injectable suspension of the present invention (G4)

FIG. 8 depicts photographs showing that solid tumors of MKN 45 cells in BALB/c nude mice were necrotized and detached 2 weeks after administration of 50 mg/head of the injectable suspension of the present invention (G2).

Figure 9:
FIG. 9 depicts photographs showing that a solid tumor of MKN-45 cells in BALB/c nude mice proliferated 2 weeks after administration of a control drug (G5).

FIG. 9 depicts photographs showing that a solid tumor of MKN-45 cells in BALB/c nude mice proliferated 2 weeks after administration of a control drug (G5).

As shown in FIGS. 5 and 9, in the vehicle control group (G1) and the control drug (G5), the tumor cells proliferated 5-fold or more, suggesting that the inhibitory effect on the proliferation of cancer cells was insignificant in the vehicle control group (G1) and the control drug (G5). In G2, G3 and G4, which have 2-fold and 4-fold differences in the initial dose of the injectable composition of the present invention, the results after 2 weeks showed similar tumor tissue necrosis and detachment patterns, indicating that the injectable suspension of the present invention does not show the change in effect with a change in the concentration (dose) thereof. This is the general characteristic of the injectable suspension of the present invention, and shows that the physical and biochemical properties and effects of the quinine salt suspension may not change depending on the concentration thereof.

Accordingly, the concentration range of the quinine salt in the injectable composition of the present invention is not limited by the formal description of the appended claims.

From the above-described results, it was found that, when the gastric cancer cell line MKN-45 was transplanted to form a solid tumor and the injectable suspension composition of the present invention was administered into the solid tumor, the groups administered with the injectable suspension composition of the present invention showed a significant decrease in the tumor volume compared to the vehicle control group (G1). Particularly, it was found that the groups (G2, G3 and G4) administered with 12.5, 25 and 50 mg/head of the injectable suspension composition of the present invention showed a significant decrease in the tumor weight compared to the vehicle control group (G1), indicating that the tumor was detached by administration of the injectable suspension composition of the present invention. This suggests that the injectable suspension composition of the present invention exhibits an anticancer effect by inducing the necrosis and detachment of a tumor.

The injectable suspension composition of the present invention has an anticancer mechanism by which the composition acts locally in a tumor tissue administered with the composition and shows a rapid antitumor effect (1-2 weeks after administration).

Therefore, it is expected that the anticancer effect of the injectable suspension composition of the present invention will be superior to the effects of conventional anticancer formulations.

As described above, the quinine salt-containing injectable anticancer composition for local administration according to the present invention shows an $IC_{50}$ value against MKN-45 cells, which is about 10 times lower than Paclitaxel, as determined by an MTT assay in vitro, suggesting that the anticancer composition has an excellent cytotoxic effect.

When the drug of the present invention is administered to tumor tissue, it changes to a solid state in the tumor tissue and acts selectively on the tumor cells without affecting the whole body, indicating that it can exhibit tumor therapeutic effects. This is a first invention related to tumor treatment with quinine hydrochloride.

Furthermore, the quinine salt is poorly soluble in water, and thus is prevented from spreading to body parts other than the affected part and does not cause adverse effects, including systemic toxicity and normal cell necrosis. Accordingly, it causes no weight loss.

In addition, the composition of the present invention may contain a contrast agent or a fluorescent probe, which makes it possible to measure the metabolic distribution of the composition in the affected area to thereby effectively administer the composition, thereby increasing the accuracy of administration of the composition.

Although the specific embodiments of the present invention have been disclosed for illustrative purposes, those skilled in the art will appreciate that various modifications, additions and substitutions are possible without departing from the scope and spirit of the invention as disclosed in the accompanying claims.

What is claimed is:

1. An injectable composition for local administration for cancer treatment, comprising, based on 100% (w/w) of the composition: 30-60 (w/w) of a quinine chloride; 1-2% (w/w) of lidocaine as a local anesthetic; 0.1-0.5⁵% (w/w) of riboflavin as an antioxidant; 0.01-0.2% (w/w) of Ioversol as a contrast agent; and the remainder saline; wherein the injectable composition is to be injected into cancer cells in a solution state by heating to a temperature of 40° C. or higher, the temperature being predetermined according to the w/w percent of the quinine chloride, and wherein the quinine chloride has a structure according to formula 1:

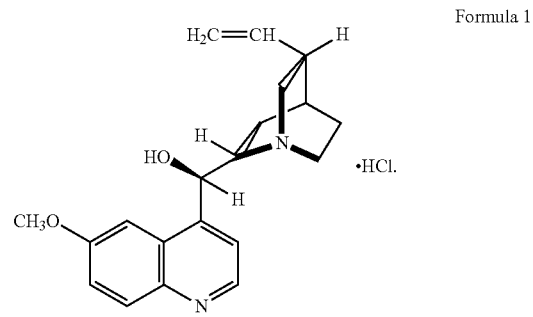

Formula 1

2. The injectable suspension composition of claim 1, wherein the content of the quinine hydrochloride in the composition is 30-50% (w/w).

3. A method of treating cancer in a patient in need thereof comprising: changing a suspension composition comprising quinine hydrochloride and saline into an injectable solution by heating the suspension to a temperature of 40° C. or higher so as to enable the quinine hydrochloride to be administered at high concentrations and act locally, the temperature being predetermined according to the w/w percent of the quinine chloride, and injecting the heated solution directly into cancer cells wherein the solution is solidified within the cancer cells as the solution cools down below a crystallization temperature of the solution by a body temperature of a cancer patient, thereby minimizing migration of the quinine hydrochloride to normal cells.

* * * * *